(12) United States Patent
Beers et al.

(10) Patent No.: US 7,030,077 B2
(45) Date of Patent: Apr. 18, 2006

(54) DETERGENT COMPOSITIONS

(75) Inventors: Olaf Cornelis Beers, Vlaardingen (NL); Rudolfus Johannes Hafkamp, Vlaardingen (NL)

(73) Assignee: Unilever Home and Personal Care USA, a division of Conopco, Inc., Greenwich, CT (US)

( * ) Notice: Subject to any disclaimer, the term of this patent is extended or adjusted under 35 U.S.C. 154(b) by 158 days.

(21) Appl. No.: 10/353,725

(22) Filed: Jan. 29, 2003

(65) Prior Publication Data

US 2003/0144161 A1 Jul. 31, 2003

(30) Foreign Application Priority Data

Jan. 29, 2002 (GB) .................................. 0202017

(51) Int. Cl.
*C11D 3/382* (2006.01)
*C11D 3/60* (2006.01)
*C11D 17/00* (2006.01)

(52) U.S. Cl. ............. 510/344; 510/349; 510/351; 510/358; 510/298; 510/438; 510/446; 510/463; 510/470

(58) Field of Classification Search ............ 510/344, 510/349, 438, 463, 446, 296, 351, 358, 298, 510/470
See application file for complete search history.

(56) References Cited

U.S. PATENT DOCUMENTS

| | | | | |
|---|---|---|---|---|
| 4,082,682 A | * | 4/1978 | Inamorato et al. ............ 510/324 |
| 4,097,418 A | | 6/1978 | Rolfes ......................... 252/531 |
| 4,369,180 A | * | 1/1983 | Mihalovits .................... 514/21 |
| 4,810,496 A | * | 3/1989 | Jensen .......................... 424/646 |
| 4,957,907 A | * | 9/1990 | McAnalley .................... 514/54 |
| 5,122,418 A | * | 6/1992 | Nakane et al. ................ 424/401 |
| 5,165,915 A | * | 11/1992 | Tokubo et al. ................ 424/63 |
| 5,258,656 A | * | 11/1993 | Pawlick ....................... 307/141 |
| 5,352,387 A | * | 10/1994 | Rahman et al. ............. 510/496 |
| 5,560,872 A | * | 10/1996 | Rahman et al. ............. 510/392 |
| 5,616,552 A | * | 4/1997 | Yoshihara et al. ........... 510/490 |
| 5,861,144 A | * | 1/1999 | Peterson et al. .............. 424/65 |
| 5,880,076 A | * | 3/1999 | Vermeer ....................... 510/123 |
| 6,043,202 A | | 3/2000 | Eriksen et al. .............. 510/119 |
| 6,376,455 B1 | * | 4/2002 | Friedli et al. ................ 510/515 |
| 6,395,701 B1 | * | 5/2002 | Connor et al. ............... 510/437 |
| 6,494,920 B1 | | 12/2002 | Weuthen et al. ................ 8/137 |
| 6,610,311 B1 | * | 8/2003 | Charambura et al. ........ 424/400 |
| 6,613,733 B1 | * | 9/2003 | Barnabas et al. ............ 510/470 |
| 6,706,679 B1 | * | 3/2004 | Bergeron et al. ............ 510/476 |
| 6,723,688 B1 | * | 4/2004 | Malik et al. ................. 510/130 |
| 2002/0103094 A1 | * | 8/2002 | Masschelein et al. ........ 510/276 |
| 2003/0032573 A1 | * | 2/2003 | Tanner et al. ................ 510/400 |

FOREIGN PATENT DOCUMENTS

| | | | |
|---|---|---|---|
| CN | 1169466 A | * | 1/1998 |
| DE | 28 43 517 | | 4/1980 |
| EP | 194 097 | | 9/1986 |
| EP | 908 171 | | 4/1999 |
| GB | 2 236 760 | | 4/1991 |
| GB | 2 358 403 | | 7/2001 |
| GB | 2 358 404 | | 7/2001 |
| JP | 61275207 A | * | 12/1986 |
| JP | 01/104700 | | 4/1989 |
| WO | 98/56975 | | 12/1998 |
| WO | 99/51714 | | 10/1999 |
| WO | 00/45788 | | 8/2000 |
| WO | 00/08129 | | 12/2000 |

OTHER PUBLICATIONS

Derwent Abstract of JP 59 016813 published Jan. 28, 1984.
Derwent Abstract of SU 1 707 058 published Jan. 23, 1992.
Derwent Abstract of JP 59 015497 published Jan. 26, 1984.
Co-pending U.S. Appl. No. 10/268,248, filed Oct. 10, 2002, Hafkamp et al.
Co-pending U.S. Appl. No. 10/268,247, filed Oct. 10, 2002, Hafkamp et al.
Co-pending U.S. Appl. No. 10/353,724, filed Jan. 29, 2003, Beers et al.
Derwent Abstract of JP 80 49172—published: Feb. 20, 1996.
Derwent Abstract of CN 1152608—published Jun. 25, 1997.
Derwent Abstract of JP 41 06200—published Apr. 8, 1992.
Derwent Abstract of JP 11 04700—published Apr. 21, 1989.

* cited by examiner

*Primary Examiner*—Lorna M. Douyon
(74) *Attorney, Agent, or Firm*—Rimma Mitelman

(57) ABSTRACT

Particulate laundry detergent compositions, especially high bulk density powders and tablets, contain low levels of aloe vera or other herbal extract beneficial to the skin. The herbal extract is preferably present in the form of coloured, preferably, green, speckles having a 1% solution pH not exceeding 9. The detergent compositions preferably contain a mild surfactant system.

22 Claims, No Drawings

DETERGENT COMPOSITIONS

TECHNICAL FIELD

The present invention relates to laundry detergent compositions, especially built granular laundry detergent compositions. The invention is especially applicable to compositions exhibiting increased mildness to the skin.

BACKGROUND

Heavy duty laundry detergent compositions have for many years contained an anionic sulphonate or sulphate surfactant, for example, linear alkylbenzene sulphonate (LAS) or primary alcohol sulphate (PAS), as the principal detergent-active ingredient. These anionic surfactants are frequently used in conjunction with ethoxylated alcohol nonionic surfactants which give improved detergency on hydrophobic soils.

These anionic and anionic/nonionic surfactant systems are robust and highly efficient on a wide range of soils and under a wide range of conditions, for example, temperature and water hardness. However, the anionic surfactants are not noted for mildness to skin. These materials are designed to interact with fatty materials like body soil and protein residues on soiled laundry, and can therefore interact with the skin to give reactions such as dryness and erythema (redness). The milder surfactants used to formulate products intended for prolonged skin contact, for example, shampoos and shower gels, would not perform adequately in heavy duty laundry detergent compositions because of insufficient interaction with fatty materials occurring as soil.

It is possible substantially to increase the mildness to skin of a laundry detergent composition containing an anionic sulphonate or sulphate detergent and a conventional detergent ethoxylated nonionic surfactant, without detriment to detergency performance, for example, by increasing the proportion of nonionic surfactant in the system, or by incorporating low levels of certain cosurfactants.

While real mildness benefits can be achieved by these means, it is not easy to communicate the concept to the consumer. The present inventors now propose that the message can be reinforced by the incorporation of aloe vera, an ingredient strongly associated in the mind of the consumer with skin benefits, desirably in a form which also provides a visual cue. Other herbal extracts known for their skin mildness benefits may also be used together with, or instead of, aloe vera.

PRIOR ART

JP 01 104 700A (Y Morita) discloses detergent or soap containing a herb or herbal extract, preferably aloe plants, for example, aloe vera L. or liliaceae. The benefits are a sterilising effect, a softening effect on textile fibres, and overcoming the problems associated with surfactants, for example, rough skin.

WO 00 45788A (Cognis) discloses a mild detergent mixture comprising ester quaternaries and aloe vera. Preferred levels of aloe vera are 1 to 10 wt % of the detergent mixture.

WO 00 08129A (Unilever C3861) discloses mild particulate laundry detergent compositions based on high-foaming anionic surfactant (for example linear alkylbenzene sulphonate) plus low levels of one or more milder cosurfactants, for example, amine oxide or cocoamidopropyl betaine.

According to our copending British Patent Applications Nos. 01 24306.2 and 01 24308.8 (Cases C4161 and C4163), the mildness to skin of detergent compositions containing anionic sulphonate surfactants may be improved by the incorporation of low levels of alkylpolyglycosides or highly ethoxylated nonionic surfactants.

Visual cues are disclosed, for example, in GB 2 258 403A and GB 2 358 404A (Unilever C3993 and C3991). Coloured speckles are very well known in the art and are disclosed, for example, in U.S. Pat. No. 4,097,418 (Procter & Gamble) and WO 99/51714A (Unilever C2030/1).

DEFINITION OF THE INVENTION

The present invention accordingly provides a particulate detergent composition, which comprises a minor amount of a herbal extract beneficial to human skin, the herbal extract being present in the form of granules comprising an aqueous solution of the herbal extract absorbed into and/or adsorbed onto a granular inorganic carrier material.

More particularly, the invention provides a particulate detergent composition which comprises a minor amount of aloe vera present in the form of granules comprising an aqueous aloe vera solution absorbed into and/or adsorbed onto a granular inorganic carrier material.

According to a preferred embodiment of the invention there is provided a granular detergent composition comprising:

(a) from 5 to 40 wt % of organic detergent surfactant,
(b) from 10 to 80 wt % of detergency builder,
(c) from 0.5 to 5 wt %, preferably from 1 to 3 wt %, of coloured granules comprising aloe vera and an inorganic carrier material, the granules providing from 0.0001 to 0.0050 wt %, preferably from 0.0005 to 0.0010 wt %, of aloe vera (on a 100 wt % dry matter basis).

DETAILED DESCRIPTION OF THE INVENTION

The Aloe Vera

As previously indicated, the compositions of the invention preferably contain aloe vera. Other herbal extracts providing skin benefits may be used alternatively, or in addition, to aloe vera.

Aloe vera is a plant extract well known to impart benefits to the skin. It is generally supplied, for example by Aloe Corporation (USA), as "10:1" aloe vera, which represents a tenfold dilution of pure juice as extracted from the plant. However, the pure juice itself contains residual water. The dry matter aloe vera content of the pure juice is approximately 50 wt %, so the dry matter aloe vera content of the commercial "10:1" material is approximately 5 wt %. In order to avoid confusion and lack of clarity, for the purposes of the present specification amounts of aloe vera are specified on a 100 wt % dry matter basis. Concentrations of aloe vera can be measured analytically by $^1$H-NMR.

Therefore, a typical detergent composition according to the invention, containing 0.015 wt % of the "10:1" compound, is deemed to contain 0.00075 wt % of aloe vera.

The Detergent Composition

Although the detergent composition of the invention may take any physical form, the invention is especially concerned with detergent compositions in particulate form, for example, powders or tablets. Especially preferred forms are powders having a bulk density of from 500 to 1000 g/l, and tablets.

The aloe vera is present in an amount of from 0.0001 to 0.0050 wt %, preferably from 0.0005 to 0.0010 wt %, on a 100 wt % dry matter basis.

This is approximately equivalent to from 0.002 to 0.1 wt %, preferably from 0.01 to 0.02, of the "10:1" compound. The detergent composition of the invention may advantageously contain other ingredients providing a mildness benefit. According to an especially preferred embodiment of the invention, as described in more detail below, the composition may have a surfactant system chosen for improved skin mildness.

For especial skin-friendliness, the composition of the invention may also be free of enzymes. However, compositions containing enzymes are also within the scope of the invention.

Aloe Vera Granules (Speckles)

Although for simplicity the disclosure that follows refers specifically to aloe vera, the use of skin-beneficial herbal extracts other than aloe vera is also within the scope of the invention. Aloe vera is highly preferred.

The amount of aloe vera present in the composition of the invention is low. It is therefore difficult to ensure accurate dosage and uniform distribution.

According to a preferred embodiment of the invention, the aloe vera is incorporated by means of granules in which the aloe vera solution is absorbed into and/or adsorbed onto a granular inorganic carrier material. The resulting granules, having a higher concentration of aloe vera, may then be incorporated in the detergent composition by dry mixing.

Preferably the granules contain from 0.005 to 0.500 wt %, more preferably from 0.01 to 0.25 wt %, of aloe vera (on a 100 wt % dry matter basis). This is equivalent to from 0.10 to 10 wt %, more preferably from 0.20 to 5.00 wt %, of the "10:1" compound.

Another problem with aloe vera is its sensitivity to alkaline hydrolysis. In a highly alkaline environment, for example, in a granule in which sodium carbonate is the carrier, it has a tendency to split off an acetate group. It is therefore preferred that the inorganic carrier material should be chosen such that the granules have a 1 wt % aqueous solution pH not exceeding 9.0, preferably not exceeding 8.5, more preferably not exceeding 8.0.

According to an especially preferred embodiment of the invention, the inorganic carrier material of the granules comprises sodium sulphate. Sodium carbonate is not preferred and is preferably absent.

The granules preferably contain from 90 to 99 wt % of the inorganic carrier material.

According to a further preferred embodiment of the invention, the granules contain a colourant which renders them visually distinct from the bulk of the composition, i.e. the granules are coloured speckles. A preferred colour is green because of its natural and herbal connotations. The green speckles containing aloe vera then provide an obvious cue to the consumer signalling mildness. A suitable green colourant is pigment green 7, typically incorporated in the granules at a level of from 0.1 to 0.5 wt %.

The granules may contain low levels of other minor ingredients. For example, a polymeric binder, preferably an acrylate or acrylate/maleate polymer, may be present, for example, at a level of from 0.1 to 1 wt %, preferably from 0.3 to 0.7 wt %.

The water content of the granules (excluding that originating from the aloe vera solution) preferably does not exceed 5 wt %.

The bulk density of the granules is not critical. It may typically range from 800 to 1500 g/litre, preferably from 900 to 1200 g/litre, more preferably from 1000 to 1100 g/litre. For powders at least, the bulk density is preferably chosen to match that of the bulk of the composition, although that is not critical.

The particle size of the granules is preferably chosen to match that of the bulk of the composition in order to minimise segregation. The average particle size is typically from 250 to 1000 micrometres, preferably from 350 to 800 micrometres, more preferably from 400 to 600 micrometres.

To achieve the desired concentration of aloe vera in the composition, and to give a visually pleasing effect, the granules are preferably incorporated in an amount of from 0.5 to 5 wt %, preferably from 1 to 3 wt %.

Mild Surfactant Systems

As previously indicated the composition of the invention advantageously contains a surfactant system which imparts to the composition increased mildness to the skin.

Using the anionic sulphonate or sulphate surfactants and ethoxylated nonionic surfactants normally employed in laundry detergents, at a given total surfactant level increased mildness may be achieved by decreasing the proportion of the anionic surfactant and increasing the proporion of the nonionic surfactant. Preferably, the ratio of anionic surfactant to nonionic surfactant does not exceed 2:1, and more preferably does not exceed 1.5:1.

A preferred built particulate laundry detergent composition according to the invention may therefore comprise:

(i) from 5 to 25 wt % of an anionic sulphonate or sulphate surfactant, (ii) from 1 to 10 wt % of an ethoxylated alcohol nonionic surfactant, the weight ratio of (i) to (ii) not exceeding 2:1 and preferably not exceeding 1.5:1, (iii) from 10 to 80 wt % of detergency builder and (iv) from 0.5 to 5 wt %, preferably from 1 to 3 wt %, of coloured granules comprising aloe vera and an inorganic carrier material, the granules providing from 0.0001 to 0.0050 wt %, preferably from 0.0005 to 0.0010 wt %, of aloe vera (on a 100 wt % basis) in the composition, (v) optionally other detergent ingredients to 100 wt %.

Alternatively or additionally, one or more mild cosurfactants may be used to replace a minor part of the main anionic/nonionic surfactant system, or supplement it.

One preferred class of mild surfactants is comprised by the alkylpolyglycosides, represented by the general formula I $$RO(R'O)_t(G)_x \qquad (I)$$

in which R is a hydrocarbyl group containing from 10 to 20 carbon atoms, R' is an alkylene group containing from 2 to 4 carbon atoms, G is a saccharide residue containing 5 or 6 carbon atoms, t is in the range of from 0 to 25 and x is in the range of from 1 to 10.

The hydrophobic group R may be aliphatic, either saturated or unsaturated, notably linear or branched alkyl, alkenyl, hydroxyalkyl or hydroxyalkenyl. However, it may include an aryl group for example alkyl-aryl, alkenyl-aryl and hydroxyalkyl-aryl. The preferred R group is an alkyl or alkenyl group having from 8 to 20 carbon atoms, more preferably from 8 to 16 carbon atoms. The most preferred R group is an alkyl group having from 12 to 14 carbon atoms.

The value of t in the general formula above is preferably zero, so that the —(RO)$_t$— unit of the general formula is absent. In that case the general formula becomes $$RO(G)_x \qquad (II)$$

If t is non-zero it is preferred that R'O is an ethylene oxide residue. Other likely possibilities are propylene oxide and glycerol residues. If the parameter t is non-zero so that R'O is present, the value of t (which may be an average value) will preferably lie in the range of from 0.5 to 10.

The group G is typically derived from fructose, glucose, mannose, galactose, talose, gulose, allose, altrose, idose, arabinose, xylose, lyxose and/or ribose. Preferably, the group G is provided substantially exclusively by glucose units.

The value x, which is an average, is usually termed the degree of polymerisation (dp). Desirably x is within the range of from 1 to 8. Preferred values of x lie within the range of from 1 to 3, especially from 1 to 1.8 and more especially from 1 to 1.6.

When x lies in the range 1 to 1.6 it is preferred that R is $C_8$ to $C_{14}$ alkyl or alkenyl. In especially preferred materials, R is $C_8$ to $C_{14}$ alkyl or alkenyl, t is zero, and x is within the range of from 1 to 1.6. Most preferably R is $C_{12}$–$C_{14}$, t is zero, and x is 1.4.

Commercially available alkylpolyglycosides suitable for use in the compositions of the invention include the Plantacare (Trade Mark) and Glucopon (Trade Mark) ranges ex Cognis Deutschland; Lutensol (Trade Mark) GD 70 ex BASF; Marlosan (Trade Mark) 24 ex Hüls; and Atlas (Trade Mark) G73500 ex ICI.

A preferred built particulate laundry detergent composition according to the invention containing an alkylpolyglycoside may comprise:
(i) from 5 to 25 wt % of an anionic sulphonate or sulphate surfactant,
(ii) from 1 to 10 wt % of an ethoxylated alcohol nonionic surfactant,
(iii) from 0.5 to 5 wt % of alkylpolyglycoside,
(iv) from 10 to 80 wt % of detergency builder and
(v) from 0.5 to 5 wt %, preferably from 1 to 3 wt %, of coloured granules comprising aloe vera and an inorganic carrier material, the granules providing from 0.0001 to 0.0050 wt %, preferably from 0.0005 to 0.0010 wt %, of aloe vera (on a 100 wt % basis) in the composition,
(vi) optionally other detergent ingredients to 100 wt %.

A second preferred class of mild surfactants is comprised by highly ethoxylated nonionic surfactants of the formula $$R_2-(-O-CH_2-CH_2)_n-OH$$

wherein $R_2$ is a hydrocarbyl chain and the average degree of ethoxylation n is from 15 to 40, preferably from 20 to 30.

The alkyl chain length may range, for example, from $C_{12}$ to $C_{20}$. In commercial materials containing a spread of chain lengths, these figures represent an average.

The alcohol may be derived from natural or synthetic feedstock.

Desirably, the highly ethoxylated alcohol nonionic surfactant is a solid at ambient temperature, so that it may conveniently be incorporated in the compositions of the invention in the form of separately admixed granules. Because these materials are solid, no carrier material is required in the granules: especially preferred granules are substantially 100 wt % pure and have a particle size within the range of from 100 to 2000 micrometres.

Where the alkyl chain is linear or only lightly branched, the chain length is preferably at least $C_{16}$, more preferably from $C_{16}$ to $C_{18}$. An example of a highly preferred material of this type is Lutensol (Trade Mark) AT25 ex BASF, which has an alkyl chain length of $C_{16}$–$C_{18}$ and an average degree of ethoxylation of 25.

Where the alkyl chain is more highly branched, for example, contains at least three methyl groups, a shorter chain length may be suitable. Another highly preferred material for use in the present invention is Lutensol (Trade Mark) TO20 ex BASF, which has a highly branched $C_{12}$ (average) alkyl chain containing on average from 3 to 4 methyl groups (including a terminal methyl group), and an average degree of ethoxylation of 20.

Both of these materials are waxy solids at ambient temperature and are available in pure granular form suitable for postdosing to detergent powder compositions.

A preferred built particulate laundry detergent composition according to the invention comprising a highly ethoxylated nonionic surfactant may comprise:
(i) from 5 to 25 wt % of an anionic sulphonate or sulphate surfactant,
(ii) from 1 to 10 wt % of an ethoxylated alcohol nonionic surfactant having an alkyl chain length of from $C_8$ to $C_{18}$ and an average degree of ethoxylation of from 3 to 10,
(iii) from 1 to 5 wt % of a highly ethoxylated alcohol nonionic surfactant having an average degree of ethoxylation of from 15 to 40,
(iv) from 10 to 80 wt % of detergency builder and
(v) from 0.5 to 5 wt %, preferably from 1 to 3 wt %, of coloured granules comprising aloe vera and an inorganic carrier material, the granules providing from 0.0001 to 0.0050 wt %, preferably from 0.0005 to 0.0010 wt %, of aloe vera (on a 100 wt % basis) in the composition,
(vi) optionally other detergent ingredients to 100 wt %.

Other Surfactants

Detergent-active compounds (surfactants) may be chosen from soap and non-soap anionic, cationic, nonionic, amphoteric and zwitterionic detergent-active compounds, and mixtures thereof. Many suitable detergent-active compounds are available and are fully described in the literature, for example, in "Surface-Active Agents and Detergents", Volumes I and II, by Schwartz, Perry and Berch. The preferred detergent-active compounds that can be used are soaps and synthetic non-soap anionic and nonionic compounds. The total amount of surfactant present is suitably within the range of from 5 to 40 wt %.

Anionic surfactants are well-known to those skilled in the art. Examples include alkylbenzene sulphonates, particularly linear alkylbenzene sulphonates having an alkyl chain length of $C_8$–$C_{15}$; primary and secondary alkylsulphates, particularly $C_8$–$C_{20}$ primary alkyl sulphates; alkyl ether sulphates; olefin sulphonates; alkyl xylene sulphonates; dialkyl sulphosuccinates; and fatty acid ester sulphonates. Sodium salts are generally preferred. Preferably the anionic surfactant is linear alkylbenzene sulphonate and/or primary alcohol sulphate. More preferably the anionic surfactant is linear alkylbenzene sulphonate.

Nonionic surfactants that may be used include the primary and secondary alcohol ethoxylates of the formula $$R_1-(-O-CH_2-CH_2)_m-OH$$

wherein $R_1$ is a $C_8$–$C_{20}$ hydrocarbyl chain, and the average degree of ethoxylation m is generally from 1 to 10, preferably from 3 to 8. The alkyl chain length is preferably in the $C_{12}$ to $C_{15}$ range.

Non-ethoxylated nonionic surfactants include alkylpolyglycosides, glycerol monoethers, and polyhydroxyamides (glucamide).

Cationic surfactants that may be used include quaternary ammonium salts of the general formula $R_1R_2R_3R_4N^+X^-$ wherein the R groups are long or short hydrocarbyl chains, typically alkyl, hydroxyalkyl or ethoxylated alkyl groups, and X is a solubilising anion (for example, compounds in which $R_1$ is a $C_8$–$C_{22}$ alkyl group, preferably a $C_8$–$C_{10}$ or $C_{12}$–$C_{14}$ alkyl group, $R_2$ is a methyl group, and $R_3$ and $R_4$, which may be the same or different, are methyl or hydroxyethyl groups); and cationic esters (for example, choline esters).

The list of surfactants is not intended to be exhaustive and the use any surfactant suitable for incorporation in particulate laundry detergent compositions falls within the scope of the present invention.

Other Detergent Ingredients

As previously indicated, detergent compositions of the invention also contain detergency builders, and may optionally contain bleaching components and other active ingredients to enhance performance and properties.

The compositions of the invention preferably also contain from 10 to 80%, more preferably from 15 to 70% by weight, of detergency builder. Preferably, the quantity of builder is in the range of from 15 to 50% by weight.

Preferably the builder is selected from zeolite, sodium tripolyphosphate, sodium carbonate, sodium citrate, layered silicate, and combinations of these.

The zeolite used as a builder may be the commercially available zeolite A (zeolite 4A) now widely used in laundry detergent powders. Alternatively, the zeolite may be maximum aluminium zeolite P (zeolite MAP) as described and claimed in EP 384 070B (Unilever), and commercially available as Doucil (Trade Mark) A24 from Ineos Silicas Ltd, UK.

Zeolite MAP is defined as an alkali metal aluminosilicate of zeolite P type having a silicon to aluminium ratio not exceeding 1.33, preferably within the range of from 0.90 to 1.33, preferably within the range of from 0.90 to 1.20. Especially preferred is zeolite MAP having a silicon to aluminium ratio not exceeding 1.07, more preferably about 1.00. The particle size of the zeolite is not critical.

Zeolite A or zeolite MAP of any suitable particle size may be used.

Also preferred according to the present invention are phosphate builders, especially sodium tripolyphosphate. This may be used in combination with sodium orthophosphate, and/or sodium pyrophosphate.

Other inorganic builders that may be present additionally or alternatively include sodium carbonate, layered silicate, amorphous aluminosilicates.

Organic builders that may be present include polycarboxylate polymers such as polyacrylates and acrylic/maleic copolymers; polyaspartates; monomeric polycarboxylates such as citrates, gluconates, oxydisuccinates, glycerol mono-di- and trisuccinates, carboxymethyloxysuccinates, carboxy-methyloxymalonates, dipicolinates, hydroxyethyliminodiacetates, alkyl- and alkenylmalonates and succinates; and sulphonated fatty acid salts.

Organic builders may be used in minor amounts as supplements to inorganic builders such as phosphates and zeolites. Especially preferred supplementary organic builders are citrates, suitably used in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %. Builders, both inorganic and organic, are preferably present in alkali metal salt, especially sodium salt, form.

As well as the surfactants and builders discussed above, the compositions may optionally contain bleaching components and other active ingredients to enhance performance and properties.

These optional ingredients may include, but are not limited to, any one or more of the following: soap, peroxyacid and persalt bleaches, bleach activators, sequestrants, cellulose ethers and esters, other antiredeposition agents, sodium sulphate, sodium silicate, sodium chloride, calcium chloride, sodium bicarbonate, other inorganic salts, proteases, lipases, cellulases, amylases, other detergent enzymes, fluorescers, photobleaches, polyvinyl pyrrolidone, other dye transfer inhibiting polymers, foam controllers, foam boosters, acrylic and acrylic/maleic polymers, citric acid, soil release polymers, fabric conditioning compounds, coloured speckles, and perfume.

Detergent compositions according to the invention may suitably contain a bleach system. The bleach system is preferably based on peroxy bleach compounds, for example, inorganic persalts or organic peroxyacids, capable of yielding hydrogen peroxide in aqueous solution. Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate. Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in an amount of from 5 to 35 wt %, preferably from 10 to 25 wt %.

The peroxy bleach compound may be used in conjunction with a bleach activator (bleach precursor) to improve bleaching action at low wash temperatures. The bleach precursor is suitably present in an amount of from 1 to 8 wt %, preferably from 2 to 5 wt %.

Preferred bleach precursors are peroxycarboxylic acid precursors, more especially peracetic acid precursors and peroxybenzoic acid precursors; and peroxycarbonic acid precursors. An especially preferred bleach precursor suitable for use in the present invention is N,N,N',N'-tetracetyl ethylenediamine (TAED). Also of interest are peroxybenzoic acid precursors, in particular, N,N,N-trimethylammonium toluoyloxy benzene sulphonate.

A bleach stabiliser (heavy metal sequestrant) may also be present. Suitable bleach stabilisers include ethylenediamine tetraacetate (EDTA) and the polyphosphonates such as Dequest (Trade Mark), EDTMP.

Although, as previously indicated, in one preferred embodiment of the invention enzymes are preferably absent, in other embodiments detergent enzymes may be present. Suitable enzymes include the proteases, amylases, cellulases, oxidases, peroxidases and lipases usable for incorporation in detergent compositions.

In particulate detergent compositions, detergency enzymes are commonly employed in granular form in amounts of from about 0.1 to about 3.0 wt %. However, any suitable physical form of enzyme may be used in any effective amount.

Antiredeposition agents, for example cellulose esters and ethers, for example sodium carboxymethyl cellulose, may also be present.

The compositions may also contain soil release polymers, for example sulphonated and unsulphonated PET/POET polymers, both end-capped and non-end-capped, and polyethylene glycol/polyvinyl alcohol graft copolymers such as Sokolan (Trade Mark) HP22. Especially preferred soil release polymers are the sulphonated non-end-capped polyesters described and claimed in WO 95 32997A (Rhodia Chimie).

Detergent Tablet Features and Ingredients

Detergent compositions of the invention in tablet form may incorporate certain additional features and ingredients of particular importance for tablets.

A tablet, unlike a powder, may be composed of two or more discrete regions having different compositions. In that case, references to percentage amounts based on the composition in the context of the present invention refer to the tablet composition as a whole. However, it is within the scope of the invention that any particular ingredient may not be present in every region of the tablet.

A tablet or a region of a tablet may contain water-soluble particles to promote disintegration. It may be preferred that such particles make up from 3 wt %, preferably from 5 or 10 wt % to 50 wt % of the composition of the tablet or region thereof.

Such soluble particles typically contain at least 50 wt % (of their own weight) of one or more materials which is other than soap or organic surfactant and which has a solubility in deionised water of at least 10 g/100 g at 20° C.

More preferably this water-soluble material is selected from either:

compounds with a water-solubility exceeding 50 g/100 g in deionised water at 20° C.; or sodium tripolyphosphate, containing at least 50% of its own weight of the phase I anhydrous form, and which is partially hydrated so as to contain water of hydration in an amount which is at least 1% by weight of the sodium tripolyphosphate in the particles.

As will be explained further below, these disintegration-promoting particles can also contain other forms of tripolyphosphate or other salts within the balance of their composition.

If the material in such water-soluble disintegration-promoting particles can function as a detergency builder, (as is the case with sodium tripolyphosphate) then of course it contributes to the total quantity of detergency builder in the tablet composition.

The quantity of water-soluble disintegration-promoting particles may be from 10 wt % up to 30 or 40 wt % of the tablet or region thereof. The quantity may possibly be from 12 wt % up to 25 or 30 wt % or more.

A solubility of at least 50 g/100 g of deionised water at 20° C. is an exceptionally high solubility: many materials which are classified as water soluble are less soluble than this. Materials of such high solubility may be used in amounts from 3 wt %, possibly from 5 wt % or 10 wt % up to 30 wt % by weight of the tablet.

Some highly water-soluble materials which may be used are listed below, with their solubilities expressed as grams of solid to form a saturated solution in 100 g of deionised water at 20° C.:

| Material | Water Solubility (g/100 g) |
|---|---|
| Sodium citrate dihydrate | 72 |
| Potassium carbonate | 112 |
| Urea | >100 |
| Sodium acetate | 119 |
| Sodium acetate trihydrate | 76 |
| Magnesium sulphate 7H$_2$O | 71 |

By contrast the solubilities of some other common materials at 20° C. are:

| Material | Water Solubility (g/100 g) |
|---|---|
| Sodium chloride | 36 |
| Sodium sulphate decahydrate | 21.5 |
| Sodium carbonate anhydrous | 8.0 |
| Sodium percarbonate anhydrous | 12 |
| Sodium perborate anhydrous | 3.7 |
| Sodium tripolyphosphate anhydrous | 15 |

Preferably this highly water soluble material is incorporated as particles of the material in a substantially pure form (i.e. each such particle contains over 95 wt % of the material). However, the said particles may contain material of such solubility in a mixture with other material, provided that material of the specified solubility provides at least 50 wt % of these particles.

A preferred material is sodium acetate in a partially or fully hydrated form.

It may be preferred that the highly water-soluble material is a salt which dissolves in water in an ionised form. As such a salt dissolves it leads to a transient local increase in ionic strength which can assist disintegration of the tablet by preventing nonionic surfactant from swelling and inhibiting dissolution of other materials.

Another possibility which is less preferred is that the said particles which promote disintegration are particles which contain sodium tripolyphosphate with more than 50% (by weight of the particles) of the anhydrous phase I form, and which is partially hydrated so as to contain water of hydration in an amount which is at least 1% by weight of the sodium tripolyphosphate.

Sodium tripolyphosphate is very well known as a sequestering builder in detergent compositions. It exists in a hydrated form and two crystalline anhydrous forms. These are the normal crystalline anhydrous form, known as phase II which is the low temperature form, and phase I which is stable at high temperature. The conversion of phase II to phase I proceeds fairly rapidly on heating above the transition temperature, which is about 420° C., but the reverse reaction is slow. Consequently phase I sodium tripolyphosphate is metastable at ambient temperature.

A process for the manufacture of particles containing a high proportion of the phase I form of sodium tripolyphosphate by spray drying below 420° C. is given in U.S. Pat. No. 4,536,377.

These particles should also contain sodium tripolyphosphate which is partially hydrated. The extent of hydration should be at least 1% by weight of the sodium tripolyphosphate in the particles. It may lie in a range from 1 to 4%, or it may be higher. Indeed fully hydrated sodium tripolyphosphate may be used to provide these particles.

The remainder of the tablet composition used to form the tablet or region thereof may include additional sodium tripolyphosphate. This may be in any form, including sodium tripolyphosphate with a high content of the anhydrous phase II form.

Suitable material is commercially available. Suppliers include Rhone-Poulenc, France and Albright & Wilson, UK.

The size of a tablet will suitably range from 10 to 160 g, preferably from 15 to 60 g, depending on the conditions of intended use, and whether it represents a dose for an average load in a domestic washing machine or a fractional part of such a dose. The tablets may be of any shape. However, for ease of packaging they are preferably blocks of substantially uniform cross-section, such as cylinders or cuboids.

The overall density of a tablet for fabric washing preferably lies in a range from 1040 or 1050 gm/litre preferably at least 1100 gm/litre up to 1400 gm/litre. The tablet density may well lie in a range up to no more than 1350 or even 1250 gm/litre.

Product Form and Preparation

Powders of low to moderate bulk density may be prepared by spray-drying a slurry. "Concentrated" or "compact" powders may be prepared by mixing and granulating processes, for example, using a high-speed mixer/granulator, or other non-tower processes. Both spray-drying and granulation give a substantially homogeneous "base powder" wherein the composition of any one granule is representative of the composition of the powder as a whole. Other desired ingredients may then be added by postdosing (dry-mixing).

Tablets may be prepared by compacting powders, especially "concentrated" powders. Once the base powder has been prepared it is usually mixed with other "post-dosed", materials, including the water-soluble disintegration-promoting particles referred to above.

The process then typically proceeds as follows. A binder is then added to the dry powder at a temperature such that it is in liquid form. The liquid and solids are mixed together in any suitable mixing device until the liquid and solids are relatively well mixed. The resultant formulation is allowed to cool and the binder, which is present on the surface of the particles and therefore present between them, solidifies. The resultant particulate formulation is then tabletted to form the compacted laundry detergent tablet.

Tabletting entails compaction of a particulate composition under applied pressure. A variety of tabletting machinery is known, and can be used. Generally it will function by stamping a quantity of the particulate composition which is confined in a die.

Tabletting may be carried out at ambient temperature or at a temperature above ambient which may allow adequate strength to be achieved with less applied pressure during compaction.

EXAMPLES

The invention is illustrated in further detail by the following non-limiting Examples, in which parts and percentages are by weight unless otherwise stated. Examples according to the invention are designated by numbers, and comparative examples by letters.

Example 1

Comparative Example A: Green Speckles

Green speckles containing aloe vera were prepared to the formulations shown in the Table below. The pH values of the granules, measured both in 1 wt % and 10 wt % aqueous solution, are also shown.

|  | 1 | A |
|---|---|---|
| Aloe vera 10:1 | 1.0 | 1.0 |
| Sodium sulphate | 94.3 | — |
| Sodium carbonate | — | 94.3 |
| Pigment Green 7 | 0.3 | 0.3 |
| 70% acrylate/30% maleate copolymer* | 0.4 | 0.4 |
| Water | 4.0 | 4.0 |
| Total | 100.0 | 100.0 |
| pH 1 wt % | 7.8 | 11.3 |
| pH 10 wt % | 7.8 | 11.4 |

*Sokalan (Trade Mark) CP5 ex BASF (Na salt)

These granules (speckles) contained 0.05 wt % of aloe vera on a 100 wt % dry matter basis.

Examples 2 to 5

Laundry Detergent Powders

Built laundry detergent powders of high bulk density were prepared to the following formulations by non-tower granulation and dry mixing techniques.

Examples 2 and 3

|  | 2 | 3 |
|---|---|---|
| Base powder |  |  |
| Linear alkylbenzene sulphonate | 7.50 | 7.50 |
| Nonionic surfactant $C_{12}$–$C_{15}$ 7EO | 5.86 | 5.86 |
| Soap | 0.54 | 0.54 |
| Acrylic/maleic copolymer | 0.99 | 0.99 |
| Zeolite MAP | 17.72 | 17.72 |
| Sodium carbonate (light) | 11.45 | 11.45 |
| Sodium sulphate | 9.23 | 9.23 |
| Sodium disilicate | 0.95 | 0.95 |
| Moisture, salts etc | 4.51 | 4.51 |
| Total base powder | 59.64 | 59.64 |
| Postdosed |  |  |
| APG granule 50%[1] | 2.00 | 2.00 |
| PAS granule[2] | 2.50 | 2.50 |
| Antifoam granule | 1.30 | 1.30 |
| Fluorescer granule | 0.85 | 0.85 |
| Sodium carbonate (dense) | 4.00 | 4.00 |
| Sodium sulphate (granular) | 4.05 | 4.46 |
| Citric acid | 2.56 | 2.56 |
| Na carbonate/silicate granules | 3.15 | 3.15 |
| TAED[3] granules (83%) | 2.75 | 2.75 |
| Sodium percarbonate | 14.46 | 13.20 |
| EDTMP[4], EHDP[5] | 1.10 | 1.10 |
| Enzymes (protease, amylase)[6,7] | — | 0.85 |
| Green speckles of Example 1 | 1.50 | 1.50 |
| Perfume | 0.13 | 0.13 |
| Total | 100.00 | 100.00 |

Weight ratio of anionic to nonionic surfactant: 1.28:1
Aloe vera content (100 wt% dry matter): 0.00075 wt%

Examples 4 and 5

|  | 4 | 5 |
|---|---|---|
| Base powder | | |
| Linear alkylbenzene sulphonate | 8.86 | 8.89 |
| Nonionic surfactant C$_{12}$–C$_{15}$ 7EO | 6.92 | 6.94 |
| Soap | 1.04 | 0.55 |
| Acrylic/maleic copolymer | 1.01 | 1.01 |
| Zeolite MAP | 21.02 | 21.08 |
| Sodium carbonate (light) | 13.01 | 13.05 |
| Sodium sulphate | 9.37 | 9.41 |
| Sodium disilicate | 0.97 | 0.97 |
| Moisture, salts etc | 5.22 | 5.24 |
| Total base powder | 67.97 | 68.19 |
| Postdosed | | |
| Antifoam granule | 1.30 | 1.30 |
| Fluorescer granule | 0.85 | 0.85 |
| Nonionic surfactant 25EO[8] | 2.10 | 2.10 |
| Bentonite clay[9] | 2.10 | 2.10 |
| Citric acid | 2.56 | 2.56 |
| Na carbonate/silicate granules | 3.15 | 3.15 |
| TAED[3] granules (83%) | 2.75 | 2.75 |
| Sodium percarbonate | 14.46 | 13.20 |
| EDTMP[4], EHDP[5] | 1.10 | 1.10 |
| Enzymes (protease[6], amylase[7]) | — | 0.85 |
| Green speckles of Example 1 | 1.50 | 1.50 |
| Perfume | 0.15 | 0.15 |
| Total | 100.00 | 100.00 |

Weight ratio of anionic to nonionic surfactant: 1.28:1
Aloe vera content (100 wt% dry matter): 0.00075 wt%

[1] granule containing 50 wt% alkylpolyglycoside (C$_{12}$–C$_{14}$, dp 1.4) on a sodium sulphate carrier
[2] primary C$_{12}$–C$_{14}$ alcohol sulphate granules (Sulfopon (Trade Mark) 1318G ex Cognis)
[3] tetraacetyl ethylenediamine
[4] ethylenediamine pentamethylene phosphonate, Ca/Na salt
[5] 1-hydroxyethane-1,1-diphosphonate, Na salt
[6] Savinase 12.0T 3250 GU/mg, 0.52%
[7] Termamyl 60T 4.3 MU/mg, 0.33%
[8] Nonionic surfactant C$_{16}$–C$_{18}$ 25E0, Lutensol (Trade Mark) AT25 ex BASF
[9] Laundrosil (Trade Mark) PR212 ex Sued-Chemie.

Example 6 and 7

Detergent Tablet Formulations

A detergent tablet was prepared by granulation, postdosing and compaction to the formulation of Example 6. Example 7 represents another possible tablet formulation within the present invention.

Examples 6 and 7

|  | 6 | 7 |
|---|---|---|
| Base powder | | |
| Linear alkylbenzene sulphonate | 6.51 | 8.10 |
| Nonionic surfactant C$_{12}$–C$_{15}$ 7EO | 5.07 | 3.55 |
| Soap | 0.74 | 0.63 |
| Zeolite MAP | 17.85 | 18.11 |
| Sodium carbonate (light) | 5.08 | 5.01 |
| Sodium carboxymethyl cellulose 68% | 0.32 | 0.36 |
| Moisture, salts etc | 3.53 | 3.24 |
| Total base powder | 39.10 | 39.00 |
| Postdosed | | |
| Sodium tripolyphosphate HPA | 38.83 | 37.02 |
| Nonionic surfactant 25EO | — | 2.00 |
| Antifoam granule | 1.94 | 2.00 |
| Fluorescer granule | 1.41 | 1.45 |
| Granular sodium disilicate (80%) | 2.45 | 2.50 |
| TAED granules (83%) | 2.72 | 2.83 |
| Sodium percarbonate | 10.68 | 10.25 |
| EDTMP | 1.21 | 1.25 |
| Green speckles of Example 1 | 1.50 | 1.50 |
| Perfume | 0.20 | 0.20 |
| Total | 100.00 | 100.00 |
| Aloe vera content (100% dry matter) | 0.00075 | 0.00075 |
| Ratio anionic:nonionic surfactant | 1.28 | 2.28 |

We claim:

1. A particulate laundry detergent composition, which comprises:
   (a) a surfactant;
   (b) a minor amount of a herbal extract beneficial to human skin, the herbal extract being present in the form of from 0.5 to 5 wt % post-dosed granules comprising an aqueous solution of the herbal extract absorbed into and/or adsorbed onto a granular inorganic carrier material.

2. A detergent composition as claimed in claim 1, wherein the herbal extract is aloe vera.

3. A detergent composition as claimed in claim 2, which comprises from 0.0001 to 0.0050 wt %, preferably from 0.0005 to 0.0010 wt %, of aloe vera based on a 100 wt % dry matter basis.

4. A detergent composition as claimed in claim 1, wherein the granules have a 1 wt % aqueous solution pH not exceeding 9.0, preferably not exceeding 8.5, more preferably not exceeding 8.0.

5. A detergent composition as claimed in claim 4, wherein the inorganic carrier material of the granules comprises sodium sulphate.

6. A detergent composition as claimed in claim 1, wherein the granules are free of sodium carbonate.

7. A detergent composition as claimed in claim 1, wherein the granules further comprise a colourant whereby they are rendered visually distinct from the bulk of the composition.

8. A detergent composition as claimed in claim 7, wherein the colourant is green.

9. A detergent composition as claimed in claim 2, wherein the granules contain from 0.005 to 0.5 wt %, preferably from 0.01 to 0.25 wt %, of aloe vera based on a 100 wt % dry matter basis.

10. A detergent composition as claimed in claim 1, wherein the granules contain from 90 to 99 wt % of the inorganic carrier material.

11. A detergent composition as claimed in claim 1, wherein the granules further comprise a polymeric binder.

12. A detergent composition as claimed in claim 1, wherein the granules are present in the composition in an amount of from 1 to 3 wt %.

13. A detergent composition as claimed in claim 1, which comprises anionic sulphonate surfactant.

14. A detergent composition as claimed in claim 1, which comprises a detergency builder.

15. A detergent composition as claimed in claim 1, wherein the surfactant comprises an anionic sulphonate or sulphate surfactant and an ethoxylated nonionic surfactant in a weight ratio not exceeding 2:1, preferably not exceeding 1.5:1.

16. A detergent composition as claimed in claim 1, wherein the surfactant comprises one or more surfactants mild to the skin.

17. A detergent composition as claimed in claim 16, wherein the surfactant comprises one or more surfactants selected from alkylpolyglycosides and highly ethoxylated alcohol nonionic surfactants having an average degree of ethoxylation of from 15 to 40.

18. A detergent composition as claimed in claim 16, wherein the surfactant comprises one or more surfactants selected from alkylpolyglycosides and highly ethoxylated alcohol nonionic surfactants having an average degree of ethoxylation of from 20 to 30.

19. A detergent composition as claimed in claim 1, which is free of enzymes.

20. A detergent composition as claimed in claim 1, which is a built particulate detergent composition in powder or tablet form comprising:
 (a) from 5 to 40 wt % of organic detergent surfactant,
 (b) from 10 to 80 wt % of detergency builder,
 (c) from 0.5 to 5 wt %, preferably from 1 to 3 wt %, of coloured granules comprising aloe vera and an inorganic carrier material, the granules providing from 0.0001 to 0.0050 wt %, preferably from 0.0005 to 0.0010 wt %, of aloe vera based on a 100 wt % dry matter basis.

21. A built particulate detergent composition as claimed in claim 20, which comprises:
 (i) from 5 to 25 wt % of an anionic sulphonate or sulphate surfactant,
 (ii) from 1 to 10 wt % of an ethoxylated alcohol nonionic surfactant,
 (iii) from 0.5 to 5 wt % of alkylpolyglycoside,
 (iv) from 10 to 80 wt % of detergency builder and
 (v) from 0.5 to 5 wt %, preferably from 1 to 3 wt %, of coloured granules comprising aloe vera and an inorganic carrier material, the granules providing from 0.0001 to 0.0050 wt %, preferably from 0.0005 to 0.0010 wt %, of aloe vera based on a 100 wt % dry matter basis,
 (vi) optionally other detergent ingredients to 100 wt %.

22. A built particulate laundry detergent composition as claimed in claim 20, which comprises:
 (i) from 5 to 25 wt % of an anionic sulphonate or sulphate surfactant,
 (ii) from 1 to 10 wt % of an ethoxylated alcohol nonionic surfactant having an alkyl chain length of from $C_8$ to $C_{18}$ and an average degree of ethoxylation of from 3 to 10,
 (iii) from 1 to 5 wt % of a highly ethoxylated alcohol nonionic surfactant having an average degree of ethoxylation of from 15 to 40,
 (iv) from 10 to 80 wt % of detergency builder and
 (v) from 0.5 to 5 wt %, preferably from 1 to 3 wt %, of coloured granules comprising aloe vera and an inorganic carrier material, the granules providing from 0.0001 to 0.0050 wt %, preferably from 0.0005 to 0.0010 wt %, of aloe vera based on a 100 wt % dry matter basis,
 (vi) optionally other detergent ingredients to 100 wt %.

\* \* \* \* \*